US011767374B2

(12) United States Patent
Ouyang et al.

(10) Patent No.: US 11,767,374 B2
(45) Date of Patent: Sep. 26, 2023

(54) METHOD AND USE OF *RADIX PUERARIAE* POLYSACCHARIDE IN PROMOTING LIPID-LOWERING ACTIVITY

(71) Applicant: JIANGXI UNIVERSITY OF TRADITIONAL CHINESE MEDICINE, Nanchang (CN)

(72) Inventors: Hui Ouyang, Nanchang (CN); Quan Wen, Nanchang (CN); WeiFeng Zhu, Nanchang (CN); YuLin Feng, Nanchang (CN); RongHua Liu, Nanchang (CN); YongMei Guan, Nanchang (CN); Kai Qian, Nanchang (CN); Hui Du, Nanchang (CN)

(73) Assignee: JIANGXI UNIVERSITY OF TRADITIONAL CHINESE MEDICINE, Nanchang (CN)

( * ) Notice: Subject to any disclaimer, the term of this patent is extended or adjusted under 35 U.S.C. 154(b) by 0 days.

(21) Appl. No.: 17/597,536

(22) PCT Filed: Mar. 8, 2021

(86) PCT No.: PCT/CN2021/079531
§ 371 (c)(1),
(2) Date: Jan. 10, 2022

(87) PCT Pub. No.: WO2021/180031
PCT Pub. Date: Sep. 16, 2021

(65) Prior Publication Data
US 2022/0259331 A1  Aug. 18, 2022

(30) Foreign Application Priority Data
Mar. 9, 2020 (CN) .......................... 202010156044.9

(51) Int. Cl.
*C08B 37/00* (2006.01)
*A61P 3/06* (2006.01)
*A61K 31/716* (2006.01)
*A61K 31/715* (2006.01)
*A61K 36/488* (2006.01)

(52) U.S. Cl.
CPC ........ *C08B 37/0003* (2013.01); *A61K 31/715* (2013.01); *A61K 31/716* (2013.01); *A61K 36/488* (2013.01); *A61P 3/06* (2018.01); *C08B 37/0006* (2013.01); *C08B 37/0009* (2013.01)

(58) Field of Classification Search
CPC ............ C08B 37/0009; C08B 37/0006; C08B 37/0003; A61K 31/716; A61K 31/715; A61K 36/488; A61P 3/06
USPC .............................. 514/54; 536/124; 127/43
See application file for complete search history.

(56) References Cited

FOREIGN PATENT DOCUMENTS

| CN | 101704904 A | 5/2010 |
| CN | 102357114 A | 2/2012 |
| CN | 110551234 A | 12/2019 |
| CN | 111004336 A | 4/2020 |
| WO | 2014016266 A1 | 1/2014 |
| WO | WO-2018202107 A1 * | 11/2018 ........... A61K 31/352 |

OTHER PUBLICATIONS

Dong et al. (International Journal of Biological Macromolecules 154 (2020) 1556-1564; Published online Nov. 13, 2019)).*
Rao et al., "PL-S2, a homogeneous polysaccharide from Radix Puerariae lobatae, attenuates hyperlipidemia via farnesoid X receptor (FXR) pathway-modulated bile acid metabolism" International Journal of Biological Macromolecules vol. 165 pp. 1694-1705 https://doi.org/10.1016/j.ijbiomac.2020.10.029 (Year: 2020).*
English machine translation of WO2018/202107, downloaded from worldwide.espacenet.com (Year: 2018).*
PubChem citation for "Puerarin", CID 5281807 (Year: 2023).*
Xiaoyue Kan, Study on hypolipidemic activity and liposomal formulation of Pueraria lobata polysaccharides, 2019, pp. 1-85, Jiangsu University.
Joseph G. Murphy, et al., Mayo Clinic Cardiology Review, 2006, pp. 942-944, Fourth Military Medical University Press.
Zhenyu Wang, et al., Bioactive component separation technology, 2015, pp. 78-80, Harbin Institute of Technology Press.
Miaoxiong Ran, et al.. Modern Chinese Medicine Cultivation, Breeding and Processing Manual, 1999, pp. 1294-1295, China Traditional Chinese Medicine Press.

* cited by examiner

*Primary Examiner* — Eric Olson
(74) *Attorney, Agent, or Firm* — Bayramoglu Law Offices LLC

(57) ABSTRACT

A preparation of a homogeneous polysaccharide from a *Radix Puerariae* aqueous extract is provided and the lipid-lowering activity of the polysaccharide is studied. It is proved through in vivo experiments that the homogeneous polysaccharide QL extracted from *Radix Puerariae* (a genuine medicinal material in Jiangxi Province) in the present disclosure has significant lipid-lowering activity, can significantly reduce a serum triglyceride content and a liver index, and can be used to develop a potential safe and effective lipid-lowering drug.

2 Claims, 5 Drawing Sheets

METHOD AND USE OF *RADIX PUERARIAE* POLYSACCHARIDE IN PROMOTING LIPID-LOWERING ACTIVITY

CROSS REFERENCE TO THE RELATED APPLICATIONS

This application is the national phase entry of International Application No. PCT/CN2021/079531, filed on Mar. 8, 2021, which is based upon and claims priority to Chinese Patent Application No. 202010156044.9, filed on Mar. 9, 2020, the entire contents of which are incorporated herein by reference.

TECHNICAL FIELD

The present disclosure belongs to the field of traditional Chinese medicines (TCMs), and relates to a polysaccharide, and in particular to a *Radix Puerariae* polysaccharide, a preparation method thereof, and use thereof in the preparation of a lipid-lowering drug.

BACKGROUND

With the improvement of people's living standards and the excessive intake of high-fat foods, more and more young people are prone to hyperlipidemia, which is also one of the main risk factors for coronary heart diseases (CHDs). TCM is playing an increasingly important role in the research on the regulation of cholesterol metabolism. Clinically, the treatment of hyperlipidemia mainly relies on western medicine statins (such as simvastatin), which requires long-term medication and will result in significant side effects, such as rhabdomyolysis. Therefore, it is efficient and targeted to search safe and effective lipid-lowering drugs from TCMs.

*Radix Puerariae* is the dried root of *Pueraria lobata* (Willd.) Ohwi of *Leguminosae*. *Radix Puerariae* is rich in mountainous areas in southern China. *Radix Puerariae* is a genuine medicinal material in Jiangxi Province and is commonly used as an antipyretic, which has the effects of clearing heat, promoting fluid, promoting eruption, invigorating vital function, and relieving diarrhea, and shows high nutritional and medicinal values. Known as "Southern *ginseng*", *Radix Puerariae* is a TCM that can serve as both a medicine and a food, which has significant health care and lipid-lowering effects in daily diet. *Radix Puerariae* is mainly used clinically for patients with dispersion-thirst and hyperlipidemia. Classical compound preparations, such as Gegen Tang and Gegen Qinlian decoction, have significant lipid-lowering effects, but specific pharmacodynamic substances are unclear.

In this study, when *Radix Puerariae* extracts are screened by an in vitro lipid-lowering activity test, it is found that the extract has significant lipid-lowering activity. The activity-oriented separation method is adopted to separate a *Radix Puerariae* polysaccharide QL with significant lipid-lowering activity and clear structure from *Radix Puerariae*. The preparation process is simple, safe, and effective. Thus, basic research data are provided for the research on the use of the *Radix Puerariae* polysaccharide for treating hyperlipidemia, and the *Radix Puerariae* polysaccharide can be subsequently used to develop safe and effective lipid-lowering drugs.

SUMMARY

The present disclosure is intended to provide an ingredient with lipid-lowering activity, and in particular relates to a method for extracting a homogeneous polysaccharide (QL) from *Radix Puerariae*, and use of the polysaccharide in the preparation of a lipid-lowering drug.

In the present disclosure, a *Radix Puerariae* extract is subjected to oriented separation to obtain a homogeneous polysaccharide, which is named as QL. It is confirmed through in vivo experiments that the *Radix Puerariae* polysaccharide has prominent lipid-lowering activity, which can significantly reduce serum triglyceride and white fat granule contents and thus can be developed into a lipid-lowering drug.

In the present disclosure, the TCM *Radix Puerariae* is the dried root of *Pueraria lobata* (Willd.) Ohwi of *Leguminosae*.

Characteristics of the *Radix Puerariae* polysaccharide QL: QL is a homopolysaccharide mainly composed of one monosaccharide, and has a molecular weight of 10 KDa to 60 KDa, a specific rotation of $[\alpha]20$ D-28.0 (c 0.5, $H_2O$), a protein content of 0.64%, no glycuronic acid, and a sugar content of 98.7%. Infrared spectrum (IR) of the polysaccharide shows typical polysaccharide absorption peaks including a hydroxyl absorption peak around 3,300 $cm^{-1}$ and a glycosyl absorption peak around 957 $cm^{-1}$, and shows no carbonyl absorption peak at 1,700 $cm^{-1}$, which is consistent with the measured glycuronic acid content. Gas chromatography-mass spectrometry (GC-MS) analysis is conducted after complete acid hydrolysis and acetyl derivatization, and it confirms that the *Radix Puerariae* polysaccharide QL is composed of glucose. In addition, after methylation, free hydroxyl blocking, and complete acid hydrolysis, GC-MS analysis is conducted, and it shows that in the *Radix Puerariae* polysaccharide QL-1, most glucose units are linked through α-1,3-Glu and a small number of glucose units are linked through terminal-Glu. The linkage mode is also confirmed by nuclear magnetic resonance (NMR) data. Two typical terminal carbon signals in the $^{13}$C-NMR low-field region are $\delta_C$ 97.1 and 100.9, where $\delta_C$ 100.9 (C-1) is the α-1,3-Glu terminal carbon signal; $\delta_C$ 97.1 (C-1') is the terminal-Glu terminal carbon signal; $\delta_C$ 61.8 is a signal peak of glucose C-6, which does not shift towards the low field, indicating that there is no linkage substitution at the position C-6; and the remaining $\delta_C$ 60-80 is the signal region of glucose C2-C5. $^1$H-NMR also gives the main terminal hydrogen signal $\delta_H$ 5.38 and the coupling constant J=2.0 Hz, indicating α linkage, and the $\delta_H$ 3.3-3.9 region is the signal region of glucose H2-H5.

The *Radix Puerariae* polysaccharide (QL) is prepared through the following steps: crushing *Radix Puerariae*, conducting extraction 3 times with 90° C. water in a solid-to-liquid ratio of 1:20, and filtering; concentrating a resulting aqueous extract solution to a density of 1.1 to 1.2, adding absolute ethanol at a volume 2 times a volume of a concentrate, and filtering to obtain a precipitate; re-dissolving the precipitate in water, removing pigments with activated carbon, and centrifuging to obtain a supernatant; lyophilizing the supernatant to obtain a crude polysaccharide;

dissolving the crude polysaccharide in distilled water under magnetic stirring, centrifuging, and adding a resulting supernatant to a macroporous resin column HP-20 for separation; eluting with pure water, a 10% ethanol solution, and a 20% ethanol solution, and collecting each eluate; combining the same eluates based on phenol-sulphuric acid chromogenic results and 490 nm detection results, and concentrating, dialyzing, and lyophilizing to obtain 3 secondary components L1, L2, and L3, where the component L2 has significant lipid-lowering activity and the highest yield and is eluted with 10% ethanol;

dissolving the L2 in distilled water, adding a resulting solution to a Sephacryl S-200 column (1.5 m×2.5 cm) for separation, eluting with distilled water, and collecting each eluate; and combining the same eluates based on phenol-sulphuric acid chromogenic results, and concentrating and lyophilizing to obtain the polysaccharide QL.

In vivo animal experiments have confirmed that the *Radix Puerariae* polysaccharide QL can significantly reduce the liver index of hyperlipidemia rats, and can be developed into a safe and effective lipid-lowering drug.

DETAILED DESCRIPTION OF THE EMBODIMENTS

Figure 1:
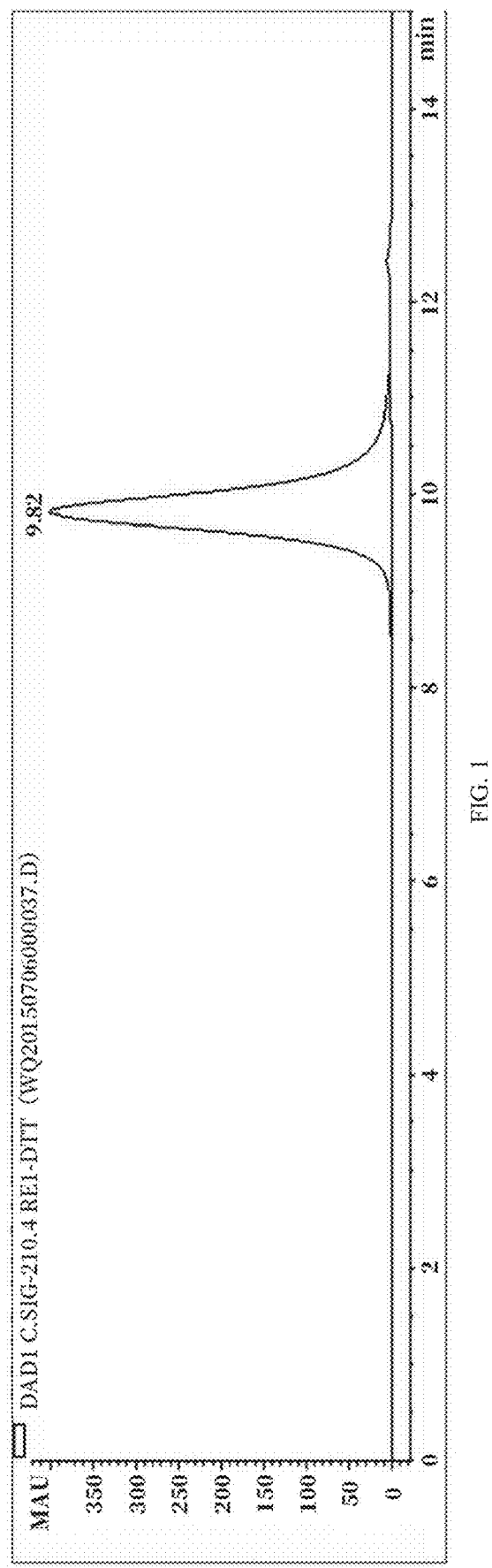
FIG. 1 shows a high-performance gel-permeation chromatography (HPGPC) chromatogram of QL (TSK-GEL GMPWXL gel column (300×7.6 mm); eluent: 0.1% NaCl; flow rate: 1.0 mL/min; and DAD 210 nm detection)
Figure 2:
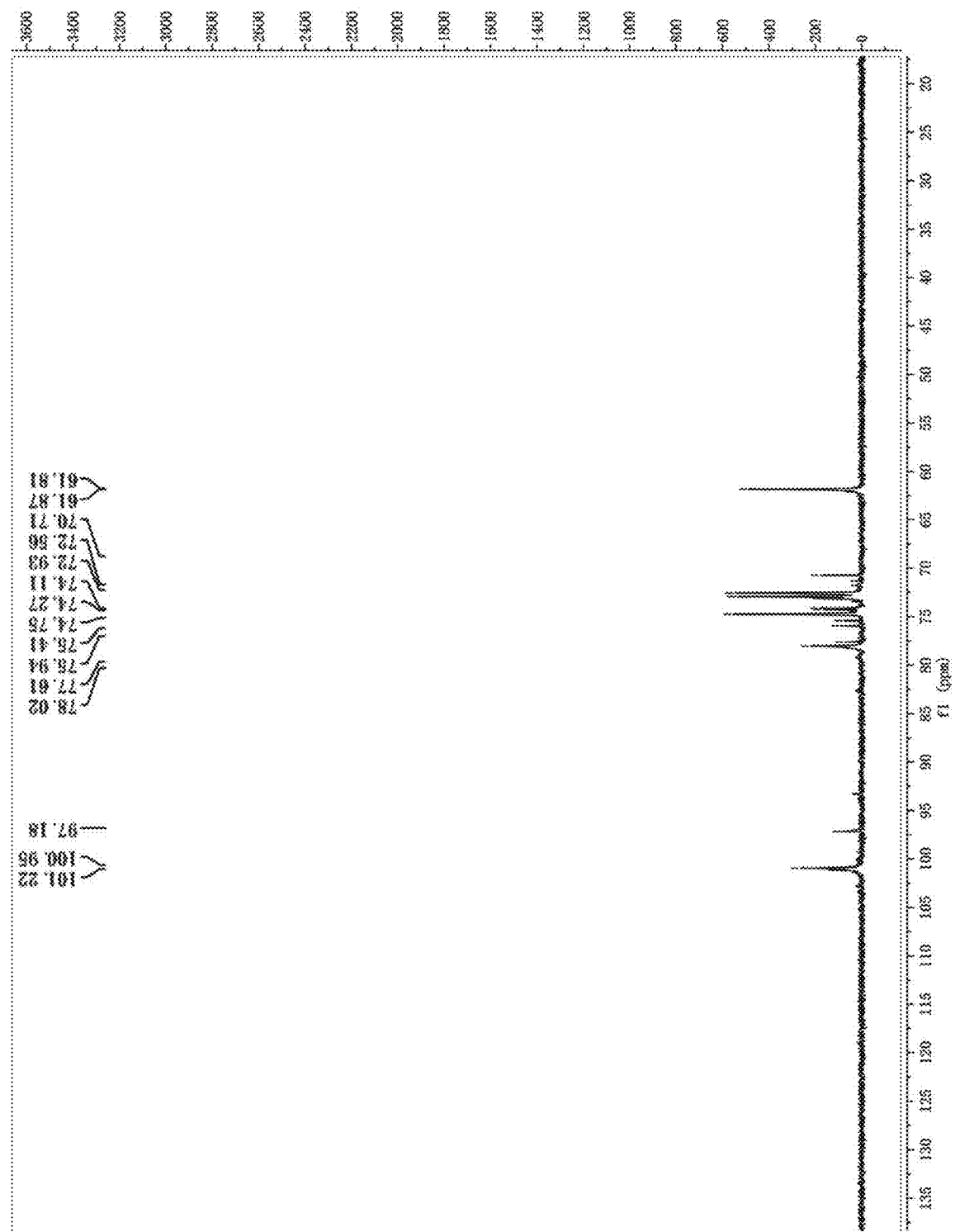
FIG. 2 is a C-NMR spectrum of the *Radix Puerariae* polysaccharide QL.
Figure 3:
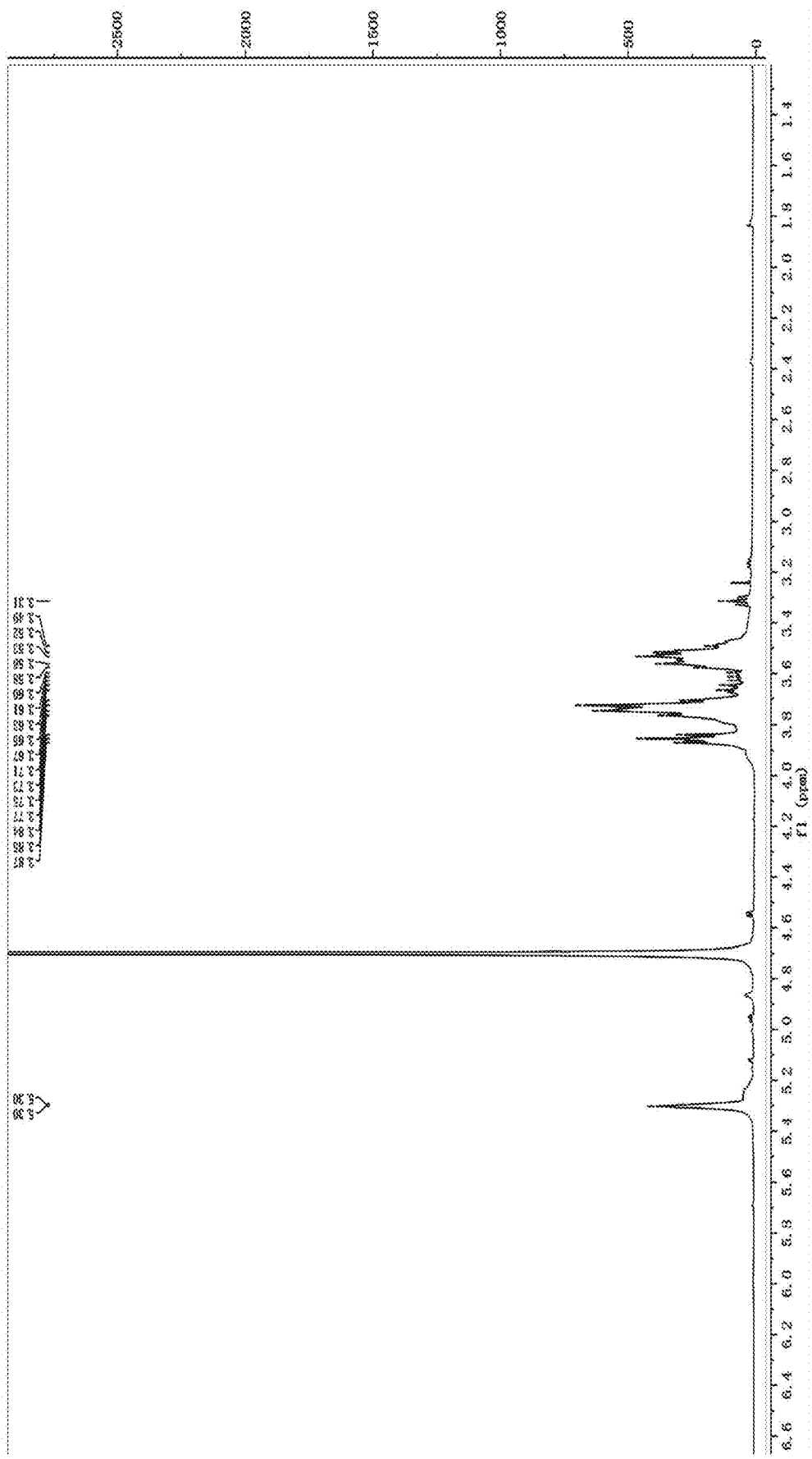
FIG. 3 is an H-NMR spectrum of the *Radix Puerariae* polysaccharide QL.
Figure 4:
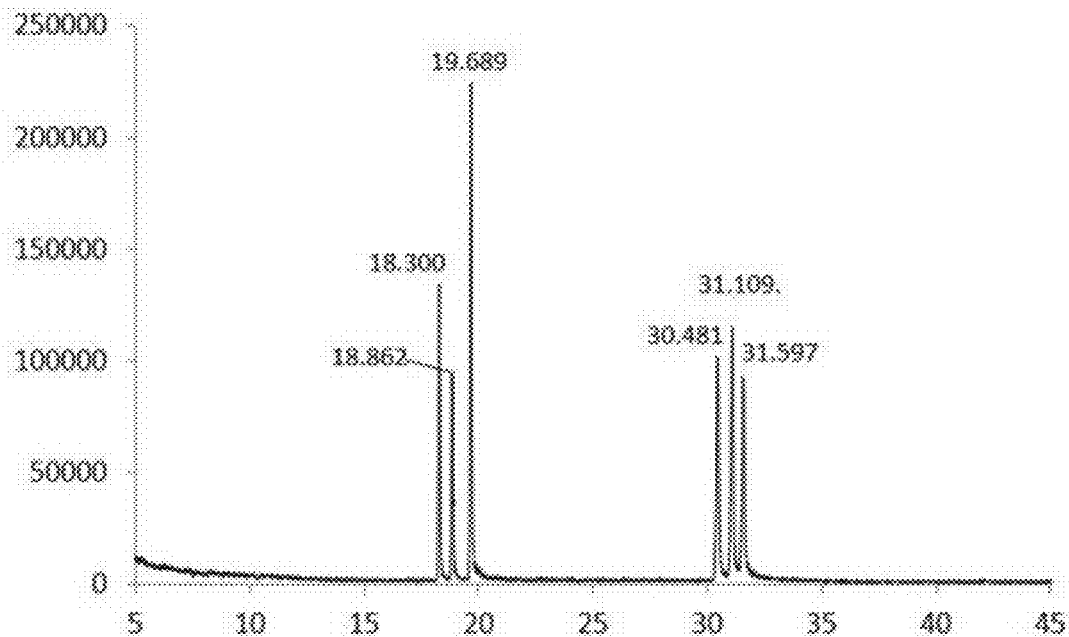
FIG. 4 is a GC-MS spectrum of monosaccharide standards [rhamnose (Rha), arabinose (Ara), xylose (Xyl), mannose (Man), glucose (Glu), and galactose (Gal) in sequence]
Figure 5:
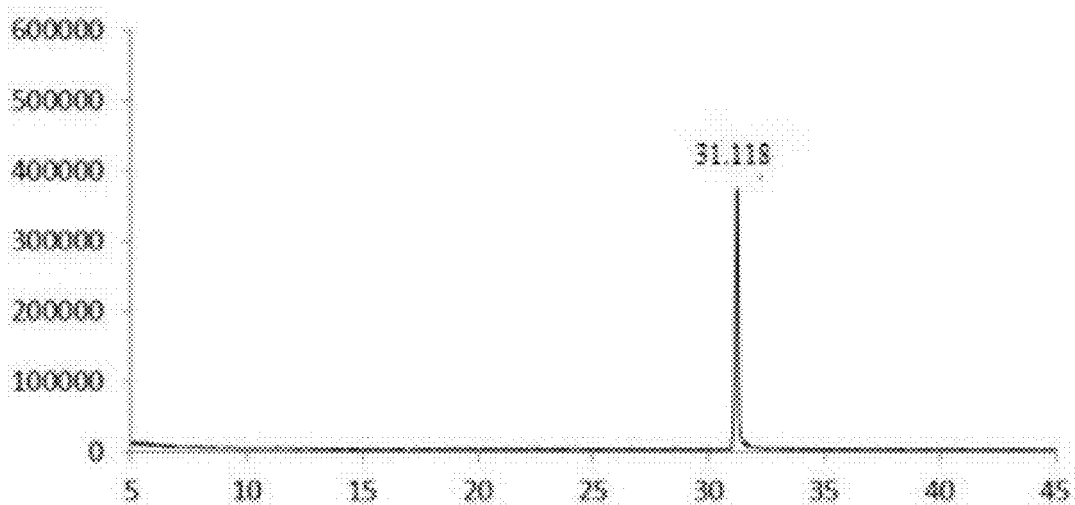
FIG. 5 is a GC-MS spectrum illustrating the monosaccharide composition of the *Radix Puerariae* polysaccharide (QL)
Figure 6:
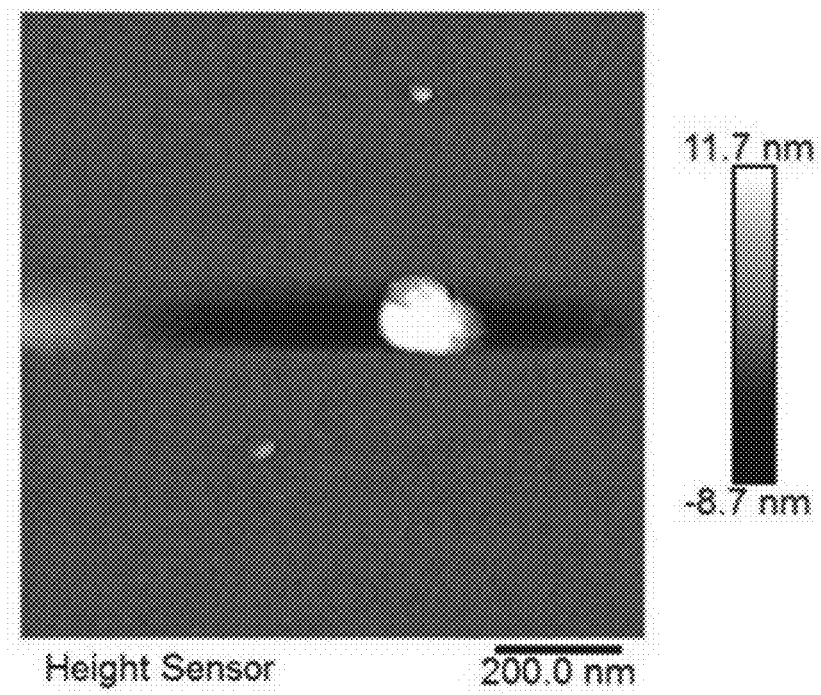
FIG. 6 is an atomic force microscopy (AFM) image of the *Radix Puerariae* polysaccharide (QL).

Example 1: Preparation of *Radix Puerariae* Polysaccharide QL 7.0 Kg of *Radix Puerariae* was crushed and then subjected to extraction 3 times with 90° C. water in a solid-to-liquid ratio of 1:20, and each resulting extraction solution was filtered; resulting extract solutions were combined and concentrated to a density of 1.1 to 1.2, then absolute ethanol was added at a volume 2 times a volume of a resulting concentrate, and a resulting mixture stood for about 3 h and filtered to obtain a precipitate; the precipitate was re-dissolved in water, then 0.1% activated carbon was added to remove pigments, and a resulting mixture was centrifuged to obtain a supernatant; the supernatant was concentrated to 0.5 L to 1 L, and then lyophilized to obtain 100 g to 244 g of a crude fluffy *Radix Puerariae* polysaccharide; 200 g of the crude polysaccharide was weighed, dissolved in distilled water under magnetic stirring, and centrifuged to obtain a supernatant; the supernatant was added to a macroporous resin column HP-20 for separation, elution was conducted with pure water, a 10% ethanol solution, and a 20% ethanol solution, and each eluate was collected; according to phenol-sulphuric acid chromogenic results and 490 nm detection results, the same eluates were combined, and then concentrated, dialyzed, and lyophilized to obtain 3 secondary components L1, L2, and L3;

the L2 eluted with 10% ethanol was dissolved in distilled water, and then added to a Sephacryl S-200 column (1.5 m×2.5 cm) for separation; elution was conducted with distilled water as an eluent and at a flow rate of about 0.8 mL/min controlled by a constant flow pump, and each eluate was collected; the phenol-sulphuric acid method was used to conduct a chromogenic reaction, and the absorbance was determined at 490 nm; and then according to the detection results, the same eluates were combined, concentrated to 0.1 L to 0.5 L, and lyophilized to obtain the polysaccharide QL.

Through HPGPC and differential detection, QL was proved to be a homogeneous polysaccharide (FIG. 1).

Example 2: Structure Characterization of *Radix Puerariae* Polysaccharide (QL)

(1) Molecular Weight Determination

The TSK-GEL GMPWXL gel column (300×7.6 mm) was adopted, with a mobile phase of 0.01 mol/L $NaNO_3$, a flow rate of 0.8 mL/min, and a column temperature of 25° C. Dextran standards with a series of molecular weights were used to determine a standard curve. The *Radix Puerariae* polysaccharide QL had a measured molecular weight of 10 KDa to 60 KDa.

(2) Determination of Total Sugar, Glycuronic Acid, and Protein Contents

The total sugar content of QL was determined by phenol-sulphuric acid method, which was 98.7%.

The glycuronic acid content of QL was determined by the meta-hydroxydiphenyl method, which was 0.0%.

The protein content of QL was determined by the Coomassie brilliant blue (CBB) method, which was 0.64%.

(3) Composition Analysis of QL

QL was hydrolyzed for 6 h with 2.0 mol/L trifluoroacetic acid (TFA) at a constant temperature of 100° C.; an appropriate amount of $NaBH_4$ was added to reduce a product obtained after complete hydrolysis, and acetylation was conducted with an acetic anhydride to prepare an alditol acetate derivative; and then the gas phase composition analysis was conducted.

QL was a homopolysaccharide mainly composed of one monosaccharide glucose, also known as glucan.

(4) Methylation Analysis

QL was methylated, and then a methylated product was depolymerized with formic acid for 4 h, hydrolyzed with 2 mol/L TFA at 100° C. for 6 h, reduced with $NaBH_4$, and acetylated with an acetic anhydride to produce a partially-methylated alditol acetate derivative; and then GC-MS analysis was conducted.

According to the determination with reference to a standard spectrum, most units in the QL were linked through α-1,3-Glu and a small number of units were linked through terminal-Glu; and this linkage mode was also confirmed by NMR data.

Example 3: In Vivo Lipid-Lowering Experimental Method 56 male Wistar rats (8 weeks old, body weight: 200 g±20 g) were purchased from Beijing Vital River Laboratory Animal Technology Co., Ltd. All animals were fed with a normal diet adaptively for 1 week. Subsequently, 8 rats were adopted as a blank control group (referred to as blank group (1)), which were fed with a normal diet; and the remaining 48 rats were fed with a high-fat diet (HF, 88.5% of ordinary rat feed, 1.2% of cholesterol, 0.3% of sodium cholate, and 10% of lard) for 2 months to construct hyperlipidemia models.

The rats were sampled every half month to determine the plasma total triglyceride (TG), total cholesterol (TC), low-density lipoprotein (LDL-C), and high-density lipoprotein (HDL-C) levels. 2 months later, all rats were anesthetized with isoflurane, and then blood samples were collected from the orbital vein using capillary tubes. The blood samples were centrifuged (4° C., 4,000 r×min$^{-1}$, and 15 min) to obtain plasma samples, a kit (purchased from Nanjing Jiancheng Biotechnology Co., Ltd., China) was used to make a standard curve, and a chromogenic reaction was conducted according to specified steps to determine the plasma TG, TC, LDL-C, and HDL-C levels, thereby determining whether hyperlipidemia models were successfully constructed.

After hyperlipidemia models were successfully constructed, the hyperlipidemia models were randomly divided into 5 groups: (2) model group; high-cholesterol diet; (3) high-dosage group: high-cholesterol diet+high-dosage intragastric *Radix Puerariae* administration (100 mg/kg); (4) medium-dosage group: high-cholesterol diet+medium-dosage intragastric *Radix Puerariae* administration (50 mg/kg); (5) low-dosage group: high-cholesterol diet+low-dosage intragastric *Radix Puerariae* administration (25 mg/kg); and (6) positive drug group: high cholesterol diet+simvastatin administration (8 mg/kg). The rats were intragastrically administered for half a month. The night before the experiment, the rats were fasted; and on the day of the experiment, the rats were weighed and resulting body weights were recorded. The rats were anesthetized with isoflurane, then blood was collected from the orbit and placed in a heparin sodium centrifuge tube, and blood samples were centrifuged (4° C., 4,000 r×min$^{-1}$, and 15 min) to obtain plasma samples. A kit (purchased from Nanjing Jiancheng Biotechnology Co., Ltd., China) was used to make a standard curve, and the plasma TG, TC, LDL-C, and HDL-C levels were determined according to specified steps. The rats were sacrificed through cervical dislocation, and then a liver tissue was collected and weighed. A liver index was calculated according to the following formula: liver index=liver weight (g)/rat weight (g).

Results showed that the high-cholesterol diet molding succeeded; the liver index of the model group was significantly increased, which was significantly different from that of other groups ($P<0.05$); the TC, TG, and LDL-C in the high-dosage, medium-dosage, and low-dosage *Radix Puerariae* polysaccharide groups showed significant differences from that of the model group, but there was no significant difference in terms of HDL-C; and there was no significant dosage-effect relationship among the high-dosage, medium-dosage, and low-dosage *Radix Puerariae* polysaccharide groups (100 mg, 50 mg, and 25 mg). Results showed that the *Radix Puerariae* polysaccharide can significantly reduce the plasma TC, TG, and LDL-C levels in hyperlipidemia rats, and the *Radix Puerariae* polysaccharide can significantly reduce the liver index in hyperlipidemia rats. Therefore, the *Radix Puerariae* polysaccharide QL can significantly reduce the TC, TG, and LDL-C contents and liver index in rat plasma, and can be developed into a lipid-lowering drug.

Data analysis: In this experiment, the SPSS11.5 version was used to analyze data (3 repetitions), and analysis of variance (ANOVA) and intergroup Duncan multiple comparison were adopted.

TABLE 1

Changes of TC, TG, LDL-C, HDL-C, and liver index in high-cholesterol hyperlipidemia rats of each treatment group

| Group | Liver index | TC (μmol/L) | TG (mg/mL) | LDL-C (mmol/L) | HDL-C (mmol/L) |
|---|---|---|---|---|---|
| (1) Blank group | 0.025 ± 0.002 b | 0.16 ± 0.04 b | 1.02 ± 0.28 b | 0.57 ± 0.13 b | 3.24 ± 0.67 a |
| (2) Model group | 0.037 ± 0.002 a | 0.38 ± 0.12 a | 1.53 ± 0.45 a | 0.78 ± 0.10 a | 2.66 ± 0.21 b |
| (3) High-dosage *Radix Puerariae* polysaccharide group | 0.029 ± 0.002 b | 0.12 ± 0.04 b | 0.94 ± 0.29 b | 0.57 ± 0.12 b | 2.83 ± 0.52 b |
| (4) Medium-dosage *Radix Puerariae* polysaccharide group | 0.028 ± 0.002 b | 0.14 ± 0.03 b | 1.06 ± 0.30 b | 0.48 ± 0.04 b | 2.57 ± 0.63 b |
| (5) Low-dosage *Radix Puerariae* polysaccharide group | 0.028 ± 0.004 b | 0.13 ± 0.03 b | 0.96 ± 0.36 b | 0.52 ± 0.05 b | 2.72 ± 0.59 b |
| (6) High-fat feed + Simvastatin | 0.027 ± 0.003 b | 0.13 ± 0.04 b | 0.87 ± 0.27 c | 0.51 ± 0.09 b | 2.89 ± 0.44 b |

Notes:
Intergroup Duncan multiple comparison (pairwise comparison) is used, and different letters indicate significant difference $P < 0.05$.

What is claimed is:

1. A method of using *Radix Puerariae* polysaccharide QL to promote lipid-lowering activity in a subject, comprising:
    preparing a therapeutically effective dosage of a *Radix Puerariae* polysaccharide QL;
    wherein, the *Radix Puerariae* polysaccharide QL is a homopolysaccharide composed of one monosaccharide glucose, and has a molecular weight of 10 KDa to 60 KDa, a protein content of 0.64%, no glycuronic acid, and a sugar content of 98.7%;
    wherein, an infrared spectrum (IR) of the *Radix Puerariae* polysaccharide QL shows typical polysaccharide absorption peaks comprising a hydroxyl absorption peak around 3,300 cm$^{-1}$, and a glycosyl absorption peak around 957 cm$^{-1}$, but shows no carbonyl absorption peak at 1,700 cm$^{-1}$, the IR of the *Radix Puerariae* polysaccharide QL is consistent with a measured glycuronic acid content;
    wherein, gas chromatography-mass spectrometry (GC-MS) analysis confirms that the *Radix Puerariae* polysaccharide QL is composed of glucose, wherein most glucose units are linked through α-1,3-Glu and a small number of glucose units are linked through terminal-Glu; and wherein, an atomic force microscopy (AFM) test shows that a spatial structure of the *Radix Puerariae* polysaccharide QL has a spherical characteristic;

administering the therapeutically effective dosage of a *Radix Puerariae* polysaccharide QL in vivo to the subject at a dosage between 25 mg/kg and 100 mg/kg.

2. The method according to claim 1, wherein the step of preparing the *Radix Puerariae* polysaccharide QL further comprises the following steps:

crushing *Radix Puerariae*, conducting an extraction 3 times with 90° C. water in a solid-to-liquid ratio of 1:20, and filtering;

concentrating a resulting aqueous extract solution to a density of 1.1 to 1.2, adding absolute ethanol at a volume 2 times a volume of a concentrate, and filtering to obtain a precipitate;

re-dissolving the precipitate in water, removing pigments with activated carbon, and centrifuging to obtain a supernatant; lyophilizing the supernatant to obtain a crude polysaccharide;

dissolving the crude polysaccharide in distilled water under a magnetic stirring, centrifuging, and adding a resulting supernatant to a macroporous resin column HP-20 for a first separation;

eluting the resulting supernatant with pure water, a 10% ethanol solution, and a 20% ethanol solution, and collecting each eluate; combining same eluates based on phenol-sulphuric acid chromogenic results and 490 nm detection results, and concentrating, dialyzing, and lyophilizing to obtain 3 secondary components;

dissolving a secondary component eluted with the 10% ethanol solution in distilled water, adding a resulting solution to a 1.5 m×2.5 cm Sephacryl S-200 column for a second separation, eluting the resulting solution with distilled water; and collecting each eluate; and combining same eluates based on phenol-sulphuric acid chromogenic results and 490 nm detection results, and concentrating and lyophilizing to obtain the *Radix Puerariae* polysaccharide QL.

* * * * *